(12) United States Patent
Chandler et al.

(10) Patent No.: US 6,192,888 B1
(45) Date of Patent: Feb. 27, 2001

(54) METHOD OF USING AN OPHTHALMIC SURGICAL SPONGE

(75) Inventors: Lamar Chandler, St. Petersburg, FL (US); James J. Salz, Encino, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/447,686

(22) Filed: Nov. 23, 1999

(51) Int. Cl.[7] ................................................. A61F 13/00
(52) U.S. Cl. ............................. 128/846; 128/858; 606/4
(58) Field of Search ................................. 128/846, 849, 128/853, 858, 890–893; 606/4, 5, 6

Primary Examiner—Michael A. Brown
(74) Attorney, Agent, or Firm—John L. Voellmicke Esq.; Alan W. Fiedler, Esq.

(57) ABSTRACT

A method of using an ophthalmic surgical sponge is described. The sponge includes a base and a corneal shield assembly. The base allows absorption of corneal fluid during eye surgery. The corneal shield assembly is used as an absorption structure and a structure to protect the corneal cap which is formed during eye surgery, particularly in surgeries that remove tissue from the corneal stroma. The corneal shield assembly protects the corneal cap as well as the hinge of the flap during the actual tissue removal from either a laser or other tissue removing means. Thus, the corneal cap is protected from scatter rays from the laser or other debris created from tissue removal of the cornea. Wetting the ophthalmic sponge creates a co-hesive seal so that the corneal shield assembly can seal the corneal cap securely. This seal is removable after the surgery is completed to re-expose the corneal cap and replace the cap on the cornea.

20 Claims, 11 Drawing Sheets

METHOD OF USING AN OPHTHALMIC SURGICAL SPONGE

FIELD OF THE INVENTION

This invention relates generally to a method of using a medical device in ophthalmic surgery. More particularly, this invention relates to a method of using a surgical ophthalmic sponge in laser refractive surgery or other similar surgery where the sponge protects the corneal cap while absorbing excess fluid and blood from the surgery.

BACKGROUND OF THE INVENTION

In the medical arts, refractive surgery is a term used for a group of various surgical procedures that alter relationships of the focusing components of the eye in an attempt to bring light to a sharp focal point on the retina without the assistance of the use of glasses or contact lenses. Possible options for refractive surgery are radial keratectomy (RK), automated lamellar keratoplasty (ALK), photorefractive keratectomy (PRK) and laser assisted in-situ keratomileusis (LASIK).

The procedure of automated lamellar keratoplasty has been performed since about 1949. However, only in recent years has it improved as a result of advancements in equipment. To treat myopia, a sophisticated instrument referred to as an automated microkeratome is used to fold back a thin superficial layer of the cornea. This layer is called the corneal cap. Under this cap, a predetermined amount of corneal tissue is removed from the center of the cornea with the microkeratome blade. The cap is then folded back into place without the need for sutures. Removal of the central corneal tissue allows flattening of the cornea thus reducing nearsightedness.

In LASIK surgery, a corneal cap is fashioned by the microkeratome as previously indicated. The reshaping of the corneal is accomplished with the laser. The bed of the cornea under the cap is flattened or re-molded to correct for areas of shortsightedness, farsightedness, and a stigmatism. After the central cornea is re-molded by the laser, the cap is folded back over the central cornea and allowed to heal in place without any need for sutures. The patient is very comfortable afterwards and can return to normal activities by the next day. Generally, sight is restored within that following day.

The drawback of these procedures, however, is that the corneal cap is unprotected during the tissue removal or re-molding portion of surgery. The corneal cap can become distorted or contaminated with excess fluid and blood during the surgery. The corneal cap needs to be kept clean and protected during the surgery.

Thus, there remains a need to provide a method that will allow excess fluid and blood to be absorbed during these types of surgery as well as protect the corneal cap prior to repositioning on the cornea.

SUMMARY OF THE INVENTION

The present invention avoids the disadvantages of the prior art by allowing the corneal cap to be protected and excess fluid and blood to be absorbed during eye surgery. Accordingly, there is provided in the present invention a method of using a surgical sponge having a base having a top, and a bottom. The ophthalmic surgical sponge also includes a corneal shield assembly. The corneal shield assembly may be part of the base or a separate component. The corneal shield assembly may have an inner flap portion, and a posterior flap portion for protecting the corneal cap during eye surgery. If the corneal shield assembly is a separate component, the corneal shield assembly is preferably attached to the base. It is not required that the assembly be attached and it may be a separate component. The corneal shield assembly could be a one-piece unitary structure or two separate pieces to comprise the anterior and posterior flap portions. The ophthalmic surgical sponge can also include a hinge that would connect the anterior flap portion to the posterior flap portion. The hinge allows the flap portions to rotate and cover the corneal cap during eye surgery. Once the ophthalmic sponge is wetted with a solution, the anterior and posterior flap portions can cohesively seal the corneal cap thereby permitting further protection. The cohesive seal is releasable and the anterior and posterior flaps can be removed to expose the corneal cap at the end of the eye surgery. This protection allows the corneal cap to avoid scatter rays and other debris from laser ablation or other tissue removal procedures. Once the corneal cap is re-exposed it is replaced back on the cornea and the operation is completed. The base allows absorption of the fluid around the cornea preventing under correction of laser ablation. The corneal shield assembly could also include a flat edge on the posterior flap portion which protects the hinge of the corneal cap. The flat edge is designed to cover the shape of the hinge of the corneal cap.

DETAILED DESCRIPTION

Figure 14:
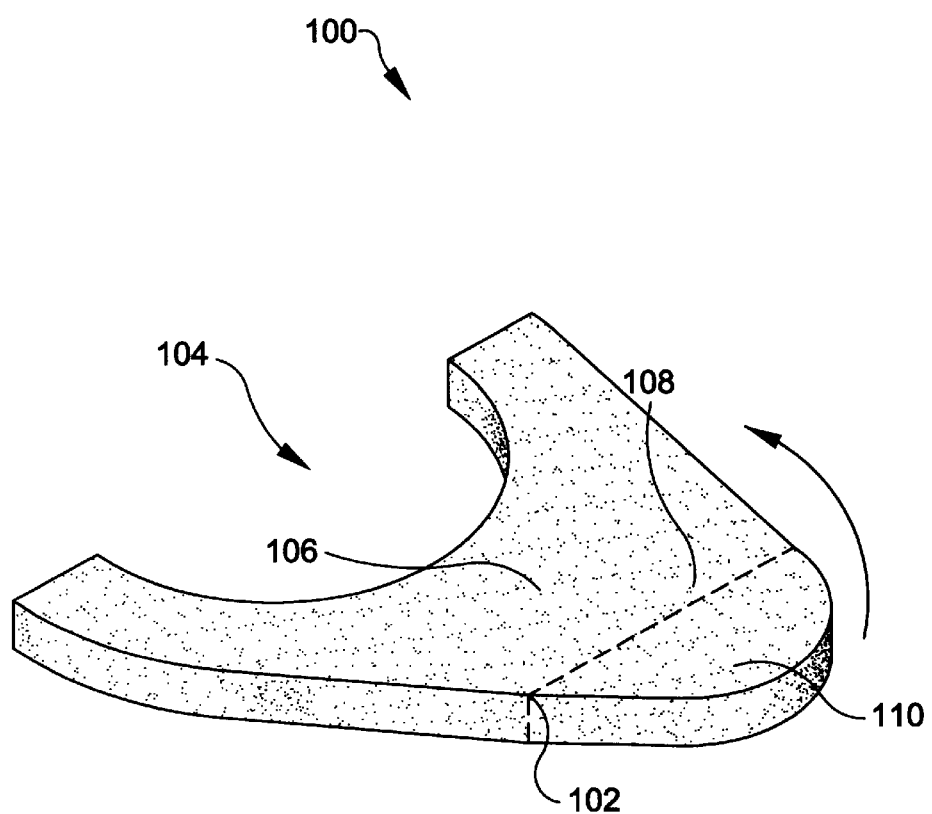
FIG. 14 is an alternate embodiment of an ophthalmic surgical sponge where the base forms the corneal shield assembly.

The ophthalmic surgical sponge for protection of a corneal cap in accordance with the subject invention is identified generally by the numeral 2 in FIGS. 1–8. In this preferred embodiment sponge 2 includes a base 4 and a corneal shield assembly 6. Base 4 and corneal shield assembly 6 can either be attached or detached from each other to provide protection of the corneal cap. In addition, the corneal shield assembly may be formed solely by the base such as shown in FIG. 14. Thus, the base may be the corneal shield assembly. Preferably, base 4 and corneal shield assembly 6 are attached and a unitary structure. However, the base and the corneal shield assembly do not need to be attached to provide the primary function of protecting the corneal cap and other structures could be provided. For example, such structures may include a separate base and a solitary detached corneal shield assembly, a base with multiple corneal shield assemblies, and a structure having a base that is the corneal shield assembly. These embodiments will be further described herein.

Figure 1:
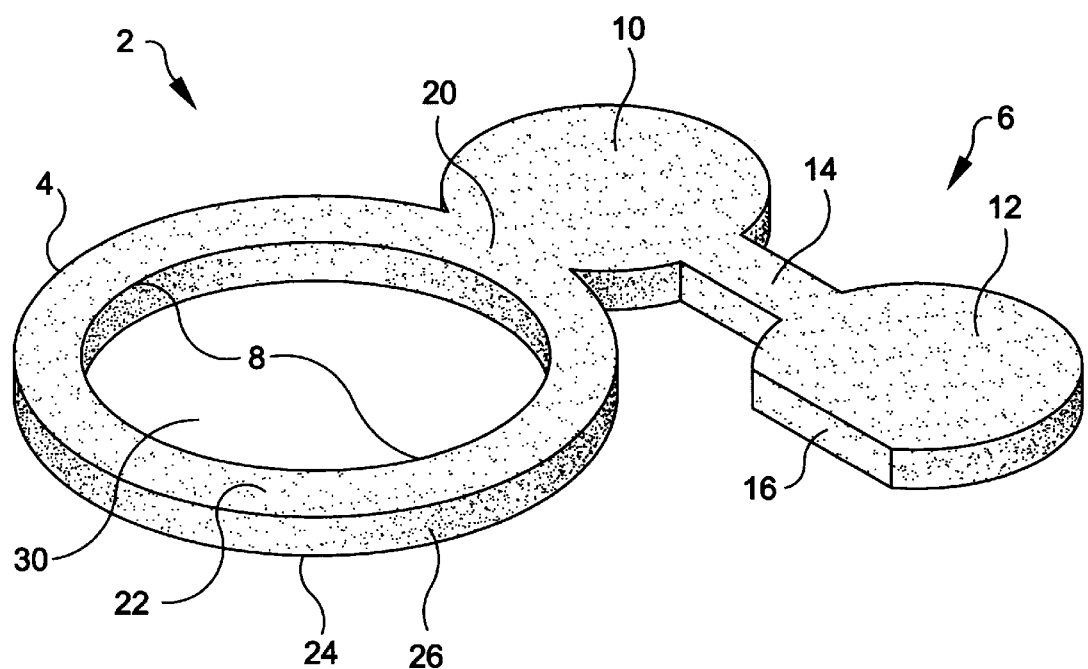
FIG. 1 is a perspective view of an ophthalmic surgical sponge of the present invention.
Figure 2:
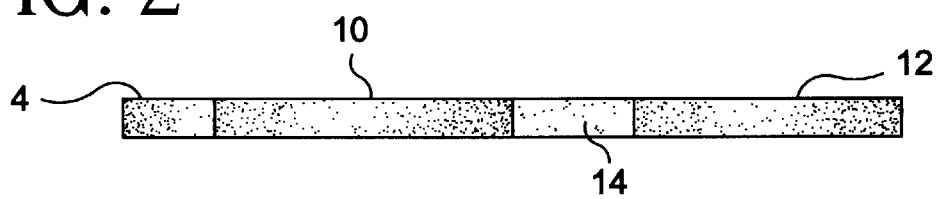
FIG. 2 is a left-sided elevational view of the sponge.
Figure 3:
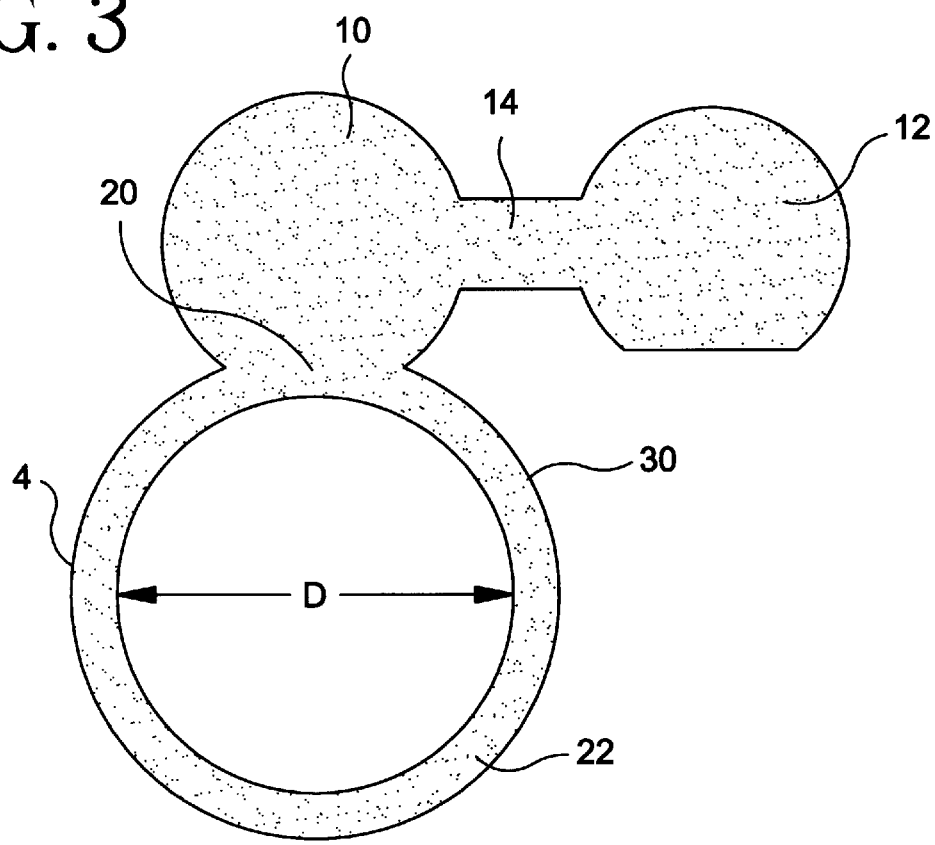
FIG. 3 is a right-side elevational view of the sponge of FIG. 1.
Figure 4:
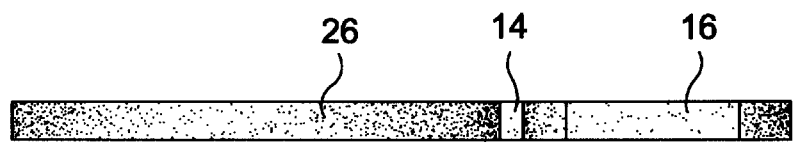
FIG. 4 is a front-elevational view of the sponge of FIG. 1.
Figure 5:
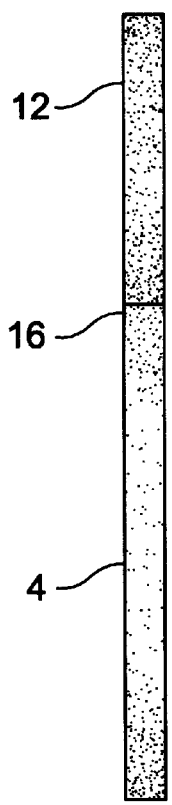
FIG. 5 is a top-plane view of the sponge of FIG. 1.
Figure 6:
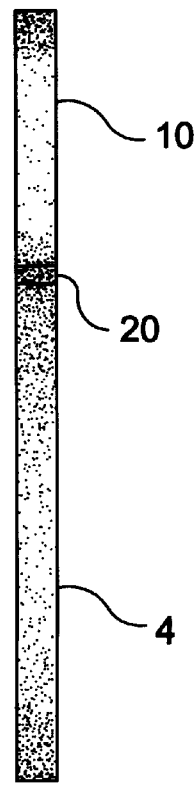
FIG. 6 is a bottom-plane view of the sponge of FIG. 1.
Figure 13:
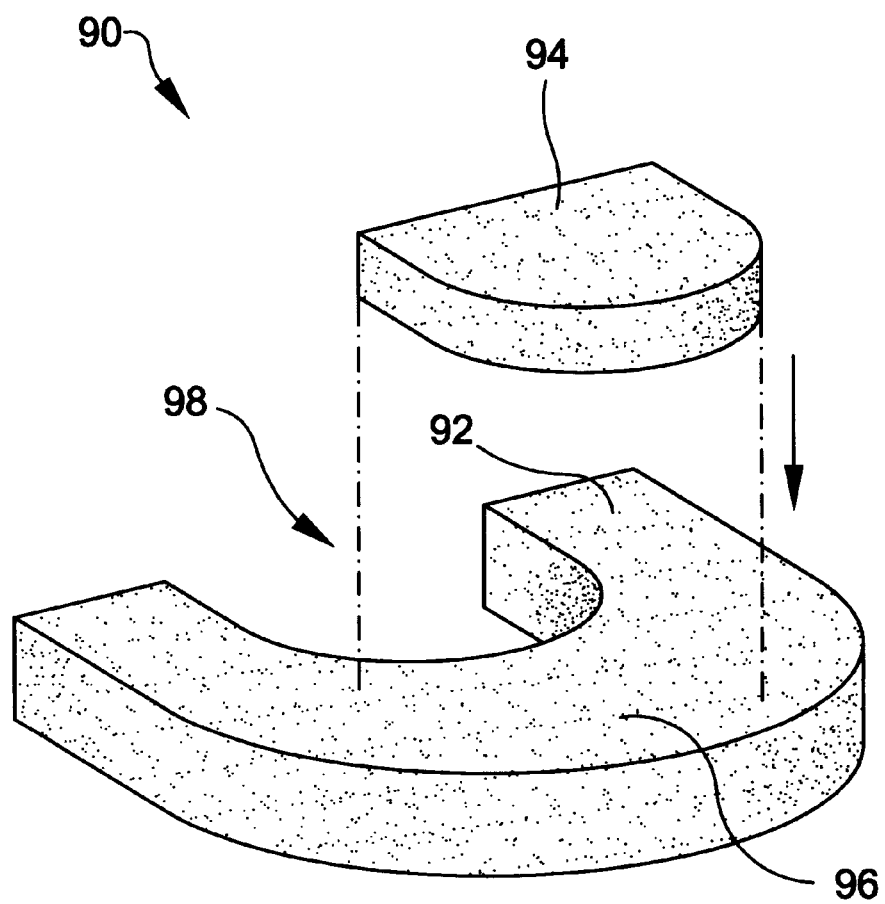
FIG. 13 is an alternate embodiment of an ophthalmic surgical sponge with the corneal shield assembly detached from the base.

Base 4 is preferably circular in shape in the form of a ring as shown in FIGS. 1 and 3. However, the base can be any geometric shape such as rectangular, semi-circle, ellipse, triangular, square and other such polygon structures. Examples of these shapes include those shown in FIG. 11, FIG. 13 and FIG. 14. Base 4 has a top 22, a bottom 24 and a side 26. The base further may include a hole 30 therethrough defined by a surface 8 that allows placement of the base on the eye such that access to the cornea is available even when the ring base is placed over the eye. The hole is not necessary as shown in FIGS. 13–14. If used, hole 30 has an inside diameter D. Inside diameter D is between about 8 mm to about 16 mm. Preferably, inside diameter D is 11 mm or 13 mm to fit the majority-sized human cornea. Preferably, base 4 is circular in shape to fit around the cornea and provide maximum operating working space to the surgeon. The base's primary function is to absorb fluid around the cornea thereby preventing undercorrection of laser ablation. However, the base does provide protection to the corneal cap.

Corneal shield assembly 6 further includes an interior flap portion 10 and a posterior flap portion 12. Again, corneal shield assembly 6 is preferably a unitary structure with base 4. However, corneal shield assembly 6 can be a separate component to the base. The corneal shield assembly can have any geometric shape including rectangular, square, triangular, semi-circle, ellipse, or any other polygon structure. However, the preferred shape of anterior flap portion 10 and posterior flap portion 12 is circular shaped to mimic the circular nature of the corneal cap.

When the corneal shield assembly is attached to ring base 4 a bridge 20 is formed between the corneal shield and the base. Bridge 20 is the location where the hinge of the corneal cap would lay during the eye surgery. Preferably, corneal shield assembly 6 further includes a hinge 14 that attaches posterior flap portion 10 to anterior flap portion 12.

Hinge 14 can be connected to anterior and posterior flap portions in any position. However, it is preferred that the hinge is centrally located between the anterior flap portion and the posterior flap portion. The hinge's primary function is to provide connection between the posterior and anterior flap portion and allow the posterior flap portion to cover the corneal cap. Preferably, hinge 14 is rectangular in shape but can assume any shape necessary to connect the posterior flap to the anterior flap portion. Additionally, hinge 14 is not required for protection of the corneal cap as later will be shown in the alternative embodiments. Hinge 14 merely provides a means of allowing the posterior flap portion to controllably and easily fold over the corneal cap which is laid on the anterior flap portion. There are other ways of providing the flexibility and motion of the posterior flap portion. For example, such means include a solitary base with a detached foldable corneal shield assembly, a foldable corneal shield assembly attached to a base, a base that is the corneal shield assembly having a foldable section, or simply two pads placed together.

Posterior flap portion further includes a flat edge 16. Flat edge 16 provides protection to the hinge of the corneal cap.

Figure 7:
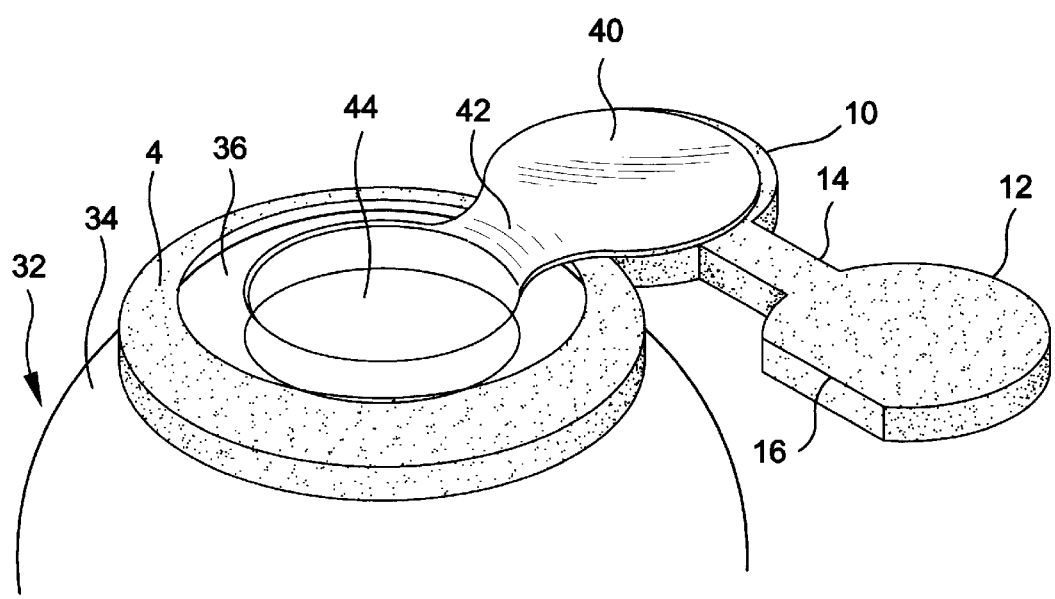
FIG. 7 is a perspective view of the sponge in FIG. 1 in use on the eye.
Figure 8:
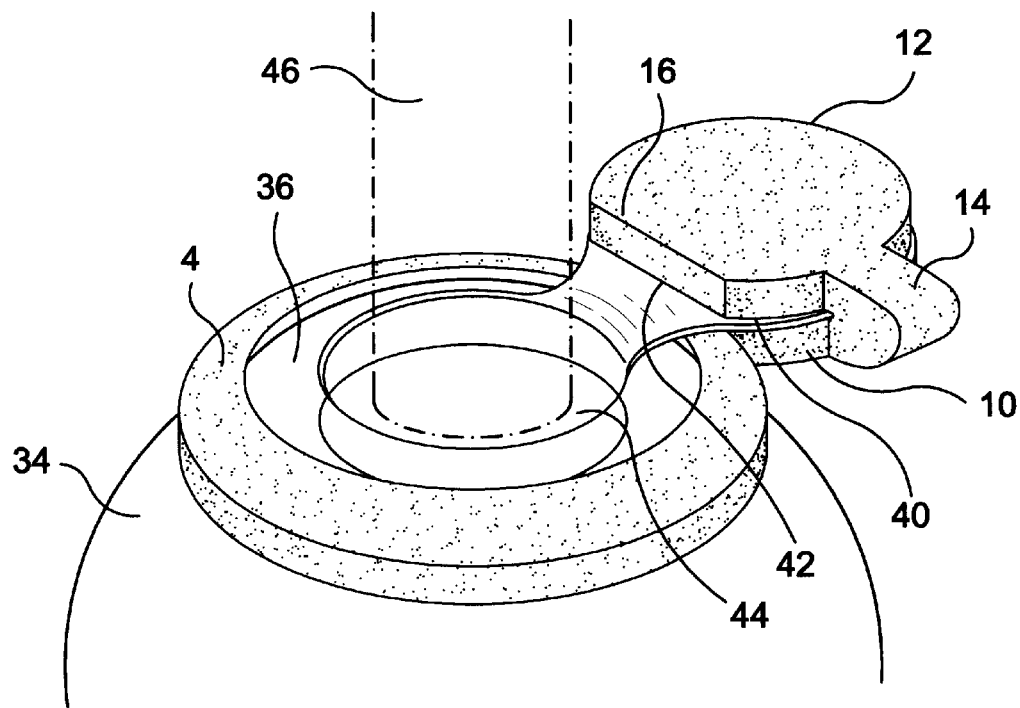
FIG. 8 is the sponge shown in FIG. 7 protecting the corneal cap during eye surgery.
Figure 9:
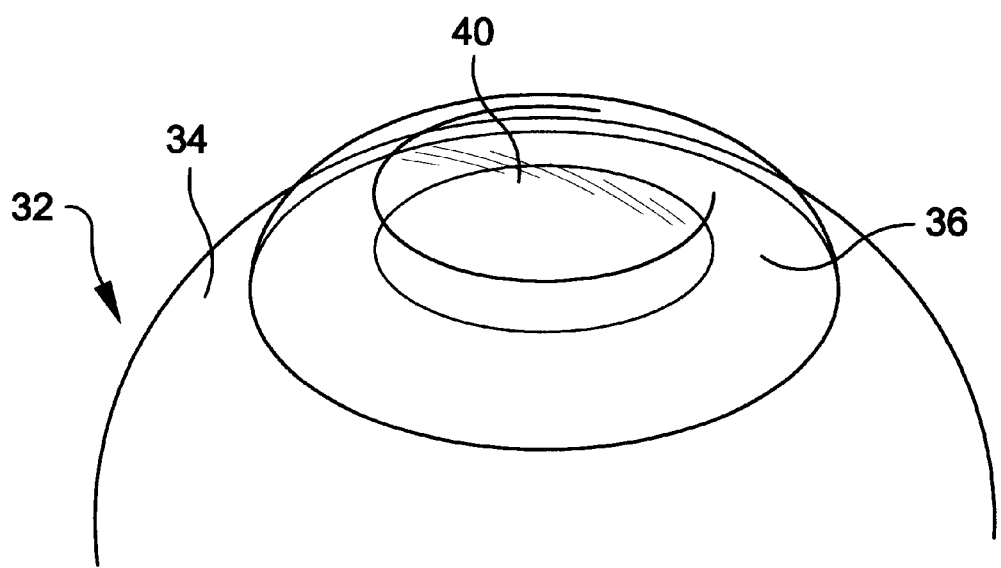
FIG. 9 is a picture of the eye after the sponge in FIG. 8 has been removed and the corneal cap replaced.

As shown in FIG. 7, corneal cap 40 lays on anterior flap portion 10 thereby exposing a corneal stroma 44. However, corneal cap may lay on the base or any portion of the corneal shield assembly. The base preferably lays in the limbus area which is located between the cornea 36 and sclera 34 of eye 32 as shown in FIG. 7. FIG. 8 illustrates protection of the corneal cap and hinge. A laser beam 46 or other instrument is used to remove tissue in the corneal stroma. Ring base 4 absorbs fluid around the cornea preventing undercorrection of laser ablation. In the preferred embodiment, the posterior flap portion is rotated over to cover the corneal cap. Depending on the structure of the ophthalmic sponge, the corneal shield assembly or base may be folded, placed, rolled and/or sealed to protect the corneal cap. Flat edge 16 covers and protects the hinge of the corneal cap 42. Thus, the corneal cap is protected from scatter rays and debris from the laser or other instrument that is actually removing the tissue of the corneal stroma. By using a wetting agent a cohesive seal is formed between the anterior and posterior flap portions. Preferably, the wetting agent is a balanced salt solution. However, other solutions can be used as a wetting agent such as normal saline solution, filtrated water, or any other type of liquid or medication. The cohesive seal can be broken and the posterior flap portion can be rotated back into its original position thereby exposing the corneal cap. After the removal of the tissue is completed, the corneal cap is replaced back on cornea 36 as shown in FIG. 9. At this point, the ophthalmic sponge is removed.

Figure 10:
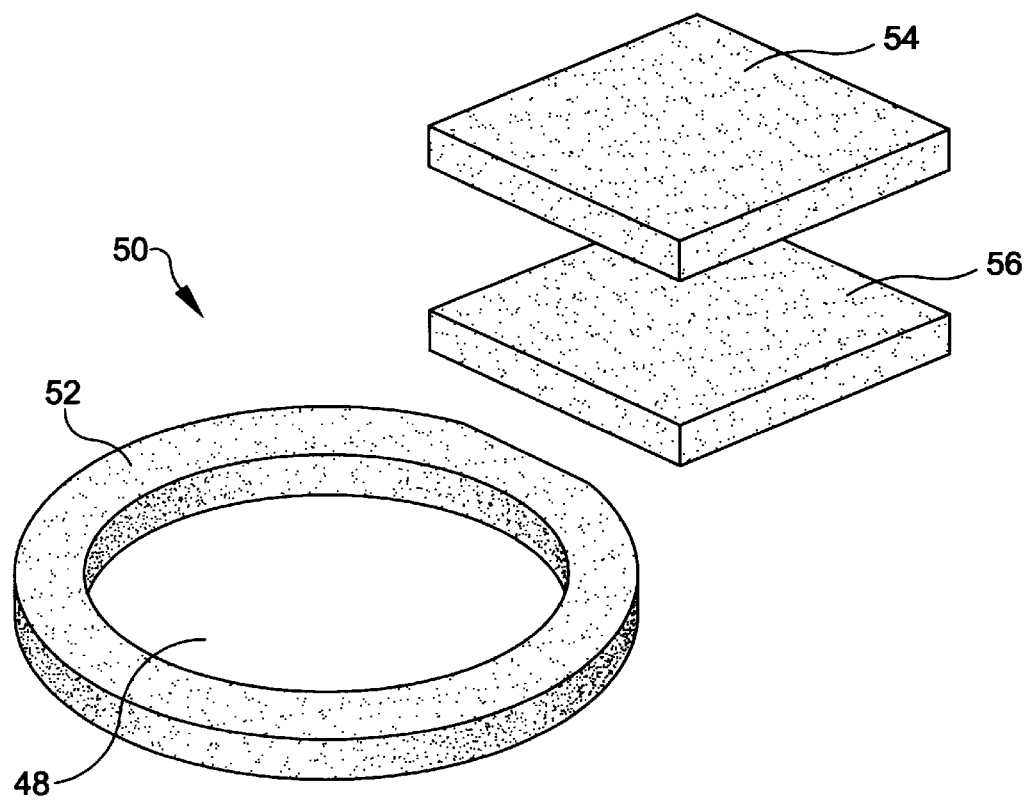
FIG. 10 is an alternate embodiment of an ophthalmic surgical sponge with the corneal shield assembly having multiple components.

The ophthalmic surgical sponge can also have alternative structures as shown in FIGS. 10–14. More particularly, an alternative embodiment of an ophthalmic surgical sponge 50 is shown in FIG. 10. Sponge 50 includes an absorption ring 52, and anterior pad 54 and a posterior pad 56. The corneal cap is placed between the pads to allow protection of the corneal cap during surgery. An eye insertion space 48 allows access to the eye. Thus, the corneal shield assembly may comprise multiple components and be detached from the base.

Figure 11:
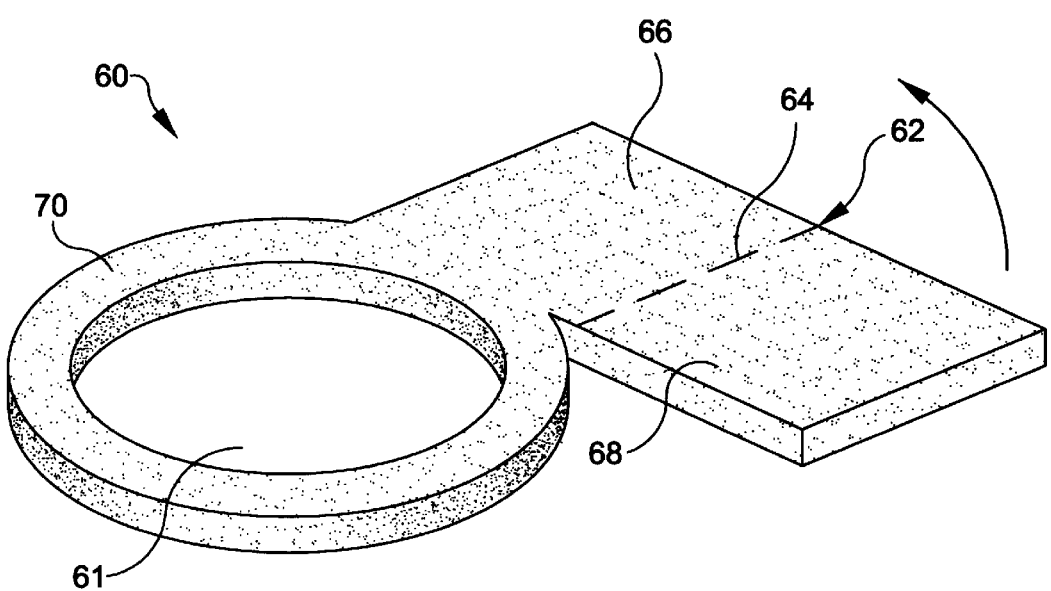
FIG. 11 is another alternate ophthalmic surgical sponge with the corneal shield assembly attached to the base.

As shown in FIG. 11, an ophthalmic sponge 60 can have a folding pad 62, either detached or as shown in FIG. 11, attached to an absorption ring 70. Pad 62 would have a front section 66 and a back section 68. The corneal cap would lay on front section 66 and back section 68 would cover the corneal cap after being folded along a folding line 64. The eye would be accessible by an eye insertion space 61. Thus, the corneal shield assembly does not require the hinge to cover and fold over the corneal cap for protection.

Figure 12:
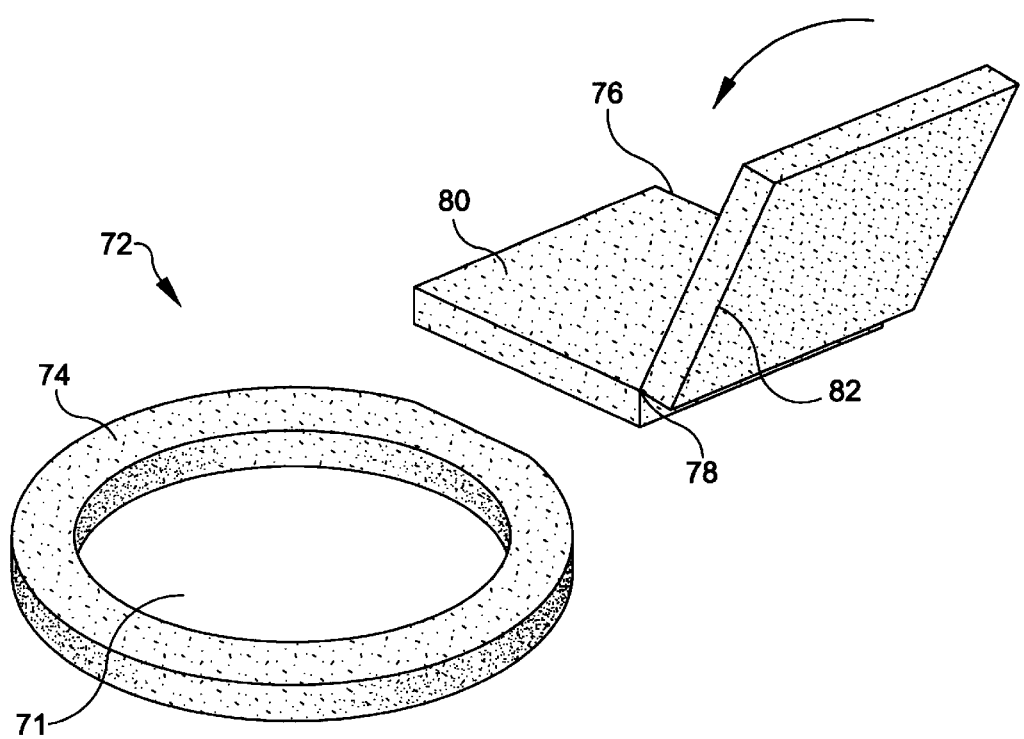
FIG. 12 is a modified version of the sponge in FIG. 11.

FIG. 12 illustrates another alternate embodiment of an ophthalmic surgical sponge 72. Sponge 72 comprises a sponge ring 74, a pad 76 that can be either attached or as shown detached to ring 74. Pad 76 can also have a cut portion 78 that would allow ease of folding pad 76 and creating a cap section 80 and a cover section 82. Cover section 82 would cover the corneal cap while the corneal cap rests on cap section 80. The eye would be accessible by an eye insertion area 71.

FIG. 13 illustrates another embodiment of an ophthalmic surgical sponge 90. Sponge 90 comprises a base 92 and a heel pad 94. Heel pad 94 can be attached or as shown detached from base 92. An eye insertion area 98 is formed by base 92. The sponge is placed adjacent to the eye. The corneal cap is laid on the base at an insertion area 96 and pad 94 is placed on the base to cover the corneal cap. Thus, the base can be various shapes such as a semi-circle.

FIG. 14 is an alternate embodiment of an ophthalmic surgical sponge 100 where a base 102 forms or is the corneal shield assembly. Base 102 forms an eye insertion area 104 to enable the sponge to be adjacent to the eye. Base 102 can be folded along a folding line 108 to cover the corneal cap after the corneal cap is placed on the base at an insertion area 106. A portion 110 of the base covers or is folded over the corneal cap to protect it during surgery. Thus, the base can be the corneal shield assembly.

Preferably, the ophthalmic surgical sponge is a unitary structure. The sponge is preferably made of a lint-resistant material. Such a lint-resistant material can be selected from the group consisting of polyvinyl alcohol, polyvinyl acetate, and combinations thereof. However, other such lint-resistant materials can be used in addition to these preferred materials. These materials are preferred due to their natural adhesion in creating a cohesive seal when wet.

Preferably, base 4 is connected to corneal shield assembly 6 at side 26. This positioning is not necessary for the corneal shield assembly to protect the corneal cap, however, it is preferred that the ophthalmic sponge is a unitary structure in order to facilitate ease of use for the surgeon and avoid a plurality of small objects surrounding the operating site.

The method of using an ophthalmic surgical sponge of the present invention for corneal cap protection is relatively straight-forward. The eye is incised to create a corneal cap 42. The first step in using the sponge is to hold the ophthalmic sponge and place the sponge adjacent to or on eye 32 adjacent to the cornea. The corneal cap is then peeled back and placed preferably on the anterior flap portion of the corneal shield assembly. However, the corneal cap may be placed on the base or other portions of the corneal shield assembly. The corneal shield assembly and/or the base can then either be wetted or used to cover the corneal cap. Preferably, the step of covering the corneal cap includes the posterior flap portion. Depending on the structure of the corneal cap assembly, the corneal cap assembly can either be folded or used to simply cover the corneal cap. In the preferred embodiment, where a hinge is utilized, the posterior flap portion is folded over to cover and protect the corneal cap. Flat edge 16 covers and protects a hinge 42 of the corneal cap from debris and laser scatter during the eye surgery. If the ophthalmic sponge is wetted, the corneal shield assembly will create a cohesive seal, sealing and protecting the corneal cap. Preferably sealing between the posterior and anterior flap portions is done. The seal is removable and the hinge allows ease of removing the posterior flap portion from the anterior flap portion thereby re-exposing the corneal cap. Alternatively, when the corneal cap is placed on the base, a seal may be created between the base and the corneal shield assembly. Additionally, if the base is the corneal shield assembly as shown in FIG. 14, then the base will form a seal with itself. The base allows absorption of fluid around the corneal during the surgery. Due to the absorptive nature of the corneal shield assembly, the anterior flap portion gives protection to the corneal cap as well as preventing conjunctive fluid from building up. In addition the anterior flap portion protects the epithelium. The posterior flap portion protects the corneal cap from scatter rays and other debris when folded over to cover the corneal cap. After the corneal cap is re-exposed, the corneal cap is placed back on the cornea, at the end of the operation, for the eye to begin healing.

The embodiments depicted in the Figures are intended to merely be exemplary and are not intended to depict all possible ophthalmic surgical sponges used for protecting the corneal cap. Rather, sponge 2 which contains ring base 4 and corneal shield assembly 6 can be used in any configuration having the appropriate dimensions and desired shape to facilitate protection of the corneal cap during eye surgery. The ability to absorb fluid from the eye and protect the corneal cap with the hinge of the corneal cap is greatly facilitated by the present invention. The present invention enables the surgeon to use a device that performs the functions of both a sponge for absorbing fluid and a shield for providing protection of the corneal cap during eye surgery.

What is claimed is:

1. A method of using an ophthalmic surgical sponge for corneal cap protection, comprising the steps of:
   (a) holding an ophthalmic sponge of the type including a base, and a corneal shield assembly; and
   (b) placing said sponge on the eye.

2. The method of claim 1 further comprising the step of placing the corneal cap on said base.

3. The method of claim 1 further comprising the step of placing the corneal cap on said corneal shield assembly.

4. The method of claim 3, wherein said corneal cap placement step further includes the step of placing the corneal cap on said anterior flap portion.

5. The method of claim 3 further comprising the step of protecting the corneal cap during eye surgery by covering the corneal cap with said corneal shield assembly.

6. The method of claim 1 further comprising the step of absorbing fluid around the cornea during eye surgery with said base.

7. The method of claim 1 further including the steps of adding a wetting agent to said ophthalmic sponge and sealing the corneal cap between said corneal shield assembly.

8. The method of claim 7 wherein said wetting agent is a balanced salt solution.

9. The method of claim 1 further including the steps of adding a wetting agent to said ophthalmic sponge and sealing the corneal cap between said base and said corneal shield assembly.

10. The method of claim 7 wherein said sealing step further includes the step of re-exposing the corneal cap.

11. The method of claim 10 further including the step of removing said ophthalmic sponge from the eye.

12. A method of using an ophthalmic surgical sponge for corneal cap protection, comprising the steps of:
   (a) holding an ophthalmic sponge of the type including a base having a top, a side and a bottom, and a corneal shield assembly having an anterior flap portion and a posterior flap portion;
   (b) placing said ophthalmic sponge on the eye such that the cornea is accessible; and
   (c) placing the corneal cap on said corneal shield assembly.

13. The method of claim 12 wherein said ophthalmic sponge placing step further includes the step of positioning said ring base on the limbus of the eye between the cornea and sclera.

14. The method of claim 12 wherein said corneal cap placing step further includes the step of placing the corneal cap on the anterior flap portion.

15. The method of claim 14 further including the step of folding said corneal shield assembly to cover the corneal cap.

16. The method of claim 15, further including the steps of adding a wetting agent and cohesively sealing the corneal cap between said anterior flap portion and said posterior flap portion.

17. A method of using an ophthalmic surgical sponge for corneal cap protection, comprising the steps of:

(a) holding an ophthalmic sponge of the type including a base shaped in the form of a circular ring having a top, a side, a bottom, and a hole having an inside diameter, and a foldable corneal shield assembly having an anterior flap portion and a posterior flap portion such that said side is mounted to said anterior flap portion, said posterior flap portion having a flat edge; and a hinge connecting said anterior flap portion to said posterior flap portion;

(b) placing said ophthalmic sponge on the eye;

(c) placing the corneal cap on said anterior flap portion; and (d) rotating said posterior flap portion and covering the corneal cap.

18. The method of claim 17 further comprising the steps of wetting said anterior and posterior flap portion and sealing the corneal cap between said flap portions.

19. The method of claim 17 further comprising the step of protecting the hinge of the corneal cap with said flat edge.

20. The method of claim 17 further comprising the steps of re-exposing the corneal cap and removing said ophthalmic sponge.

* * * * *